United States Patent [19]

Perrior et al.

[11] Patent Number: 4,990,512
[45] Date of Patent: Feb. 5, 1991

[54] PYRIDYL-PYRIMIDONES

[75] Inventors: Trevor R. Perrior, Barkham; Alan J. Whittle, Twyford; David J. Tapolczay, Reading, all of England

[73] Assignee: Imperial Chemical Industries PLC, London, England

[21] Appl. No.: 385,446

[22] Filed: Jul. 27, 1989

[30] Foreign Application Priority Data

Aug. 4, 1988 [GB] United Kingdom ............... 8818560

[51] Int. Cl.$^5$ .................. C07D 401/04; A01N 43/54
[52] U.S. Cl. .................................... 514/269; 544/310; 544/300; 544/316; 544/317; 544/319; 544/320; 544/321; 514/272; 514/274
[58] Field of Search .................. 514/269, 272, 274; 544/310, 300, 316, 317, 319, 320, 321

[56] References Cited

U.S. PATENT DOCUMENTS 4,783,466  11/1988  Katoh et al. .................. 544/333
4,873,248  10/1989  Katoh et al. .................. 544/333
4,904,714  2/1990   Raynor et al. ................ 544/310

FOREIGN PATENT DOCUMENTS 1035097  6/1966  United Kingdom .
1035098  6/1966  United Kingdom .

OTHER PUBLICATIONS

Metwally et al., Chemical Abstracts, vol. 101, Abstract No. 55039d (1984).
Kulshreshtha et al., Chemical Abstracts, vol. 96, Abstract No. 35188b (1982).
Giammanco et al., Chemical Abstracts, vol. 73, Abstract No. 3883h (1970).

Primary Examiner—John M. Ford
Attorney, Agent, or Firm—Cushman, Darby & Cushman

[57] ABSTRACT

An insecticidal compound of formula (I):

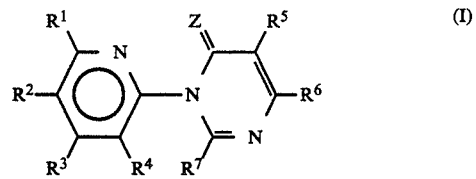

wherein $R^1$ and $R^3$ are independently selected from hydrogen; halogen; nitro; cyano; or alkyl, alkoxy, alkylthio or cycloalkyl any of which can be optionally substituted by halogen; $R^2$ is hydrogen; halogen; nitro; cyano; alkyl, alkoxy or alkylthio any of which may be optionally substituted with halogen; or $S(O)_nR^8$, where $R^8$ is alkyl, haloalkyl or cycloalkyl and n is 0, 1 or 2;

$R^4$ is hydrogen; halogen; nitro; cyano; or alkyl, alkoxy or alkythio any of which may be optionally substituted with halogen; $R^5$ is hydrogen; halogen; nitro; cyano; alkyl, alkoxy alkylthio any of which can be optionally substituted with halogen; or $NR^9R^{10}$ where $R^9$ and $R^{10}$ are independently selected from hydrogen, alkyl or cycloalkyl; $R^6$ is hydrogen; halogen; nitro; cyano; alkyl, alkoxy or alkylthio any of which can be optionally substituted with halogen; or $S(O)_nR^8$;

$R^7$ is hydrogen; halogen; nitro; cyano; alkyl; alkoxy or alkythio any of which is optionally substituted with halogen; $S(O)_nR^8$; or $NR^9R^{10}$; and Z is oxygen or sulphur.

9 Claims, No Drawings

PYRIDYL-PYRIMIDONES

PYRIDYL-PRYIMIDONES

The present invention relates to novel pyridyl pyrimidinone derivatives which have insecticidal activity to processes for their preparation and to their use as insecticides.

Pyridyl pyridone derivatives have been known hitherto as insecticides (see for Example EP-A-272824).

According to the present invention there is provided a compound of formula (I)

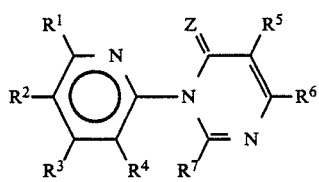

wherein $R^1$ and $R^3$ are independently selected from hydrogen; halogen; nitro; cyano; or alkyl, alkoxy, alkylthio or cycloalkyl any of which can be optionally substituted by haloqen;

$R^2$ is hydrogen; halogen; nitro; cyano; alkyl, alkoxy or alkylthio any of which may be optionally substituted with halogen; or $S(O)_n R^8$ where $R^8$ is alkyl, haloalkyl or cycloalkyl and n is 0, 1 or 2;

$R^4$ is hydrogen; halogen; nitro; cyano; or alkyl, alkoxy or alkythio any of which may be optionally substituted with halogen;

$R^5$ is hydrogen; haloqen; nitro; cyano; alkyl, alkoxy alkylthio any of which can be optionally substituted with halogen; or $NR^9 R^{10}$ where $R^9$ and $R^{10}$ are independently selected from hydrogen, alkyl or cycloalkyl;

$R^6$ is hydrogen; halogen; nitro; cyano; alkyl, alkoxy or alkylthio any of which can be optionally substituted with halogen; or $S(O)_n R^8$;

$R^7$ is hydrogen; haloqen; nitro; cyano; alkyl; alkoxy or alkythio any of which is optionally substituted with haloqen; $S(O)_n R^8$; or $NR^9 R^{10}$; and Z is oxygen or sulphur.

Suitably $R^1$, $R^2$, $R^3$, $R^4$, $R^5$, $R^6$ and $R^7$ are independently selected from hydrogen; halogen; nitro; cyano; or alkyl, alkoxy or alkylthio any of which are optionally substituted with halogen.

Suitably halogen groups for $R^1$, $R^2$, $R^3$, $R^4$, $R^5$, and $R^7$ and substituents for alkyl, alkoxy or alkylthio groups include fluoro, chloro or bromo.

Suitably alkyl, alkoxy or alkylthio groups are straight or branched chains having up to carbon atoms, preferably up to 6 carbon atoms. They suitably contain up to 6 halo substituents. Specific examples of such groups include trifluoromethyl, trifluoromethoxy, trifluoromethylthio and pentafluoroethyl.

Suitable cycloalkyl groups contain from 3 to 7 ring carbon atoms.

In a preferred embodiment of the compounds of formula (I), $R^1$, $R^3$ and $R^4$ are independently selected from hydrogen, halogen, nitro, cyano or halo substituted alkyl and $R^2$ is any of those groups and may also be alkoxy or alkylthio. In addition $R^5$, $R^6$ and $R^7$ are independently selected from hydrogen, halogen, alkoxy or alkylthio with $R^5$ being additionally selected from cyano and nitro and $R^6$ being additionally selected from haloalkyl or cyano.

Suitably $R^1$ and $R^3$ are independently selected from hydrogen or halogen such as chloro and are preferably both hydrogen.

Particularly suitable groups $R^2$ are halogen such as chloro or alkyl substituted by halogen, in particular trifluoromethyl.

Suitably $R^4$ is halogen such as chloro, or bromo, cyano, nitro or haloalkyl such as dichloromethyl.

Suitably $R^5$ and $R^7$ are independently selected from hydrogen, halogen such as bromo, or cyano and are preferably both hydrogen.

Suitably $R^6$ is halogen or alkyl substituted with halogen in particular trihalomethyl such as trifluoromethyl or pentahaloethyl such as pentaluoroethyl.

Preferably Z is oxygen.

Examples of compounds of formula (I) are set out in Table I below.

TABLE I

| COMPOUND NO. | $R^1$ | $R^2$ | $R^3$ | $R^4$ | $R^5$ | $R^6$ | $R^7$ | Z |
|---|---|---|---|---|---|---|---|---|
| 1 | H | $CF_3$ | H | Cl | H | $CF_3$ | H | O |
| 2 | H | $CF_3$ | H | H | H | $CF_3$ | H | O |
| 3 | H | $CF_3$ | H | $NO_2$ | Br | $CF_3$ | H | O |
| 4 | H | $CF_3$ | H | $NO_2$ | H | $CF_3$ | H | O |
| 5 | H | $CF_3$ | H | H | H | $C_2F_5$ | H | O |
| 6 | H | $CF_3$ | H | Cl | H | $C_2F_5$ | H | O |
| 7 | H | $CF_3$ | H | H | Br | $CF_3$ | H | O |
| 8 | Cl | Cl | H | $CHCl_2$ | H | $CF_3$ | H | O |
| 9 | H | $CF_3$ | H | Cl | Br | $CF_3$ | H | O |
| 10 | H | $CF_3$ | H | Cl | Br | $C_2F_5$ | H | O |
| 11 | H | $CF_3$ | H | CN | H | $CF_3$ | H | O |
| 12 | H | $CF_3$ | H | Br | H | $CF_3$ | H | O |
| 13 | H | $CF_3$ | H | Br | H | $C_2F_5$ | H | O |

Compounds of formula (I) can be prepared by reacting a compound of formula (II)

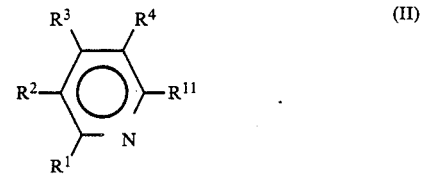

wherein $R^1$, $R^2$, $R^3$ and $R^4$ are as defined in relation to formula (I) and $R^{11}$ is a leaving group;
with a compound of formula (III)

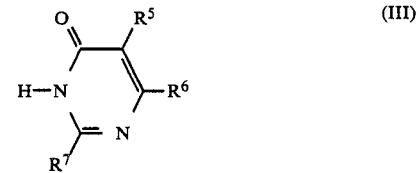

wherein $R^5$, $R^6$ and $R^7$ are as defined in relation to formula (I); and thereafter if desired converting a group $R^1$–$R^7$ to a different such group.

The reaction is suitably carried out in the presence of a solvent and a base. The base may be for example an alkali metal hydride, an alkali metal alkoxide or an alkal metal carbonate, and the solvent may be a hydrocarbon solvent, such as petroleum ether, an alcohol or an aprotic polar solvent such as dimethylformamide or dimethylacetamide.

Suitable leaving groups $R^{11}$ include halo groups such as fluoro, chloro, bromo or iodo, triflate, mesylate or tosylate.

If necessary an appropriate catalyst such as a crown ether or copper can be added depending upon the precise nature of $R^{11}$.

Preferably in the compound of formula (III), $R^7$ is hydrogen and if desired this is converted to a different group $R^7$ after coupling. Conversion of a group $R^1$-$R^7$ to a different such group may be carried out by conventional methods. In particular compounds of formula (I) wherein $R^1$, $R^2$, $R^3$, $R^4$, and/or $R^6$ is nitro can be converted into the corresponding compound of formula (I) where $R^1$, $R^2$, $R^3$, $R^4$ and/or $R^6$ is halo by reduction of the nitro group to an amino group to form a compound of formula (IV):

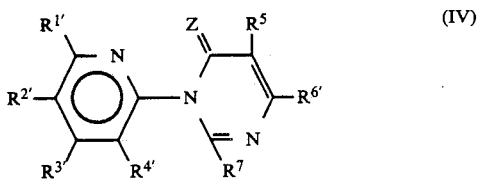

(IV)

wherein $R^{1'}$, $R^{2'}$, $R^{3'}$, $R^{4'}$, and, $R^{6'}$, are amino or are equivalent to $R^1$, $R^2$, $R^3$, $R^4$, and $R^6$ as defined in relation to formula (I) respectively provided that at least one of $R^{1'}$, $R^{2'}$, $R^{3'}$, $R^{4'}$, and $R^{6'}$, is amino and $R^5$, $R^7$ and Z are as defined in relation to formula, (I); and thereafter converting the amino group $R^{1'}$, $R^{2'}$, $R^{3'}$, $R^{4'}$, and/or $R^{6'}$, to halo. Compounds of formula (IV) are novel and as such form a further aspect of the invention.

Reduction of the nitro group to form a compound of formula (IV) can be carried out by reacting the compound with a reducing agent such as stannous chloride in acid condition, for example, in a solution in concentrated hydrochloric acid. Moderate temperatures of from 2 to 45° C. are suitably employed.

Alternatively the compound can be reduced by reaction with "hydrogen reduced" iron in a mixture of isopropanol and water, in the presence of an acid. Temperatures of from 50–100° C. preferably about 70° C. are suitably employed. Subsequent halogenation may be carried out by reaction with t-butylnitrite and a copper halide salt such as copper (I) iodide. This step is suitably carried out in an organic solvent such as acetinitrile at low temperatures of from −20° C. to +20° C. preferably at about 0° C.

Compounds of formula (I) where $R^5$ or $R^7$ are amino can be prepared by reduction of the compound of formula (I) where $R^5$ or $R^7$ is nitro as described above. Similarly compounds of formula (I) where $R^5$ or $R^7$ is halo can be prepared by halogenation of the corresponding compound where $R^5$ or $R^7$ is amino, also as described above.

The conversion of groups $R^1$-$R^7$ t different such groups may be carried out on the compounds of formula (II) and (III) prior to coupling if desired. This may produce intermediates for example were nitro groups $R^1$, $R^2$, $R^3$, $R^4$, and $R^6$ are converted to amino groups prior to halogenation. The methods for a conversion of this type is suitably the same as described above in relation to the equivalent conversions on the compounds of formula (I).

Conversion of the group $R^5$ from hydrogen into a halogen group such as bromine or chloro can be carried out by reacting the compound of formula (I) where $R^5$ is hydrogen with a halogen such as bromine in the presence of a base such as sodium acetate. The reaction is suitably carried out in an organic solvent such as acetic acid at moderate temperatures of from 0–50° C., conveniently at ambient temperature.

Alternatively the conversion can be carried out using other known halogenating agents such as N-bromosuccinimide or N-chlorosuccinimide in an organic solvent such as acetonitrile or dimethylformamide. Suitably elevated temperatures of from 60 to 100° C. are employed.

Further details of the processes for preparation of the compounds may be ascertained from the Examples set out hereinafter.

Certain compounds of formula (II) and (III) are either known compounds or they can be prepared from known compounds by known methods.

For example, compounds of formula (III) can be prepared by reacting a compound of formula (V)

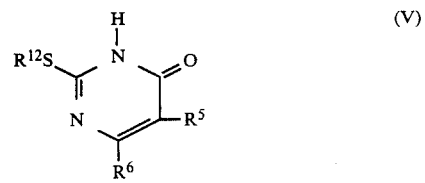

(V)

wherein $R^{12}$ is hydrogen or $C_{1-4}$ alkyl such as ethyl with Raney Nickel in an appropriate solvent such as aqueous ammonia.

Compounds of formula (V) are either known or they can be prepared from known compound by known methods (see for example A Giner-Sorolla, A Bendick: J.Am. Chem, Soc, 1958, 80, 5744).

Some compounds of formula (III) and (V) are described and claimed in copending U.S. application Ser. No. 07/341,920, filed Apr. 24, 1989. These include compounds of formula (IIIA):

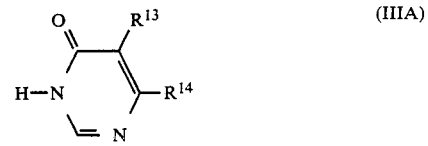

(IIIA)

wherein $R^{13}$ is hydrogen, halogen or cyano and $R^{14}$ is halo or haloalkyl with the proviso that (a) when $R^{13}$ is cyano, $R^{14}$ is other than chlorine; (b) $R^{13}$ and $R^{14}$ are not both halo; (c) when $R^{13}$ is halo, $R^{14}$ is other than monofluoromethyl; and (d) when $R^{13}$ is hydrogen, $R^{14}$ is not halo or a halomethyl group.

A particular example of $R^{14}$ is pentafluoroethyl.

Compounds of formula (IIIA) can be prepared by various routes including preparation from the appropriate compound of formula (V) as described above. Alternatively the compound of formula (IIIA) can be prepared from the appropriate compound of formula (III) where $R^5$ is hydrogen by halogenation using for example conditions similar to those described above in relation to the conversion of $R^5$ from hydrogen to halogen.

Compounds of formula (IIIA) where $R^{13}$ is cyano can be prepared by reacting a compound of formula (III) where $R^5$ is bromine with a cyanide salt such as copper (I) cyanide in an organic solvent such as quinoline at elevated temperatures of from 200 to 250° C.

Compounds of formula (V) described in Ser. No. 07/341,920 are compounds of formula (VA):

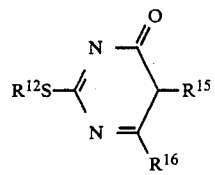

wherein $R^{12}$ is as defined in relation to formula (V), $R^{15}$ is cyano and $R^{16}$ is $R^6$ as defined in relation to formula (I) or $R^{15}$ is hydrogen or halogen other than fluorine and $R^{16}$ is pentafluoroethyl or difluoromethyl.

Compounds of formula (VA) can be prepared by treating a compound of formula (VII):

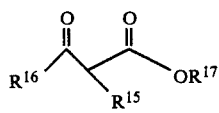

wherein $R^{15}$ and $R^{16}$ are as defined in relation to formula (VA) and $R^{17}$ is a $C_{1-6}$ alkyl group with thiourea or an appropriate alkylated derivative thereof in the presence of a strong base such as an alkali metal alkoxide such as sodium methoxide. Elevated temperatures of from 60° C. to 90° C. are suitably employed.

Some compounds of formula (II) are novel compounds and these form a further aspect of the invention. In particular in accordance with the invention there is provided a compound of formula (IIA):

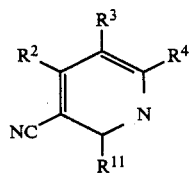

wherein $R^2$, $R^3$ and $R^4$ are as defined in relation to formula (I) and $R^{11}$ is as defined in relation to formula (II).

Compounds of formula (IIA) where $R^{11}$ is halogen are prepared by halogenation of a compound of formula (VIII):

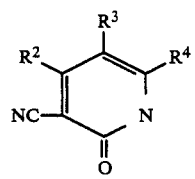

wherein $R^2$, $R^3$, $R^4$ are as defined in relation to formula (I). The reaction is suitably effected using a conventional halogenating agent such as phoshorus pentachloride, phosphonyl chloride or a mixture thereof. Elevated temperatures of from 90 to 140° C. are suitably employed. Compounds of formula (VIII) can be prepared by reacting a compound of formula (IX):

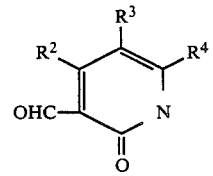

with hydroxylamine hydrochloride and an alkali metal formula such as sodium formate. A solvent such as formic acid is suitably employed and the reaction is preferably effected at elevated temperatures of from 90 to 110° C.

Compounds of formula (IX) are known compounds or they can be prepared from known compounds by known methods.

The compounds of formula (I) may be used to combat and control infestations of insect pests and also other invertebrate pests, for example, acarine pests. The insect and acarine pests which may be combatted and controlled by the use of the invention compounds include those pests associated with agriculture (which term includes the growing of crops for food and fibre products), horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The composition may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts or aliphatic monoesters of sulphuric acid, for example sodium lauryl sulphate, salts of sulphonated aromatic compounds, for example sodium dodecylbenzesulphone, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable orqanic solvents are dimethyl formamide, ethylene dichloride, isopropyl alcohol, propylene glycol and other qlycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proporation of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous prepartion containing between 0.0001% and 0.1% by weight of the active ingredient (approximately equivalent to from 5–2000 g/ha) is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required.

Examples of suitable insecticides include the following:
(a) Pyrethroids such as permethrin, esfenvalerate, deltamethrin, cyhalothrin in particular lambda cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3furylmethyl-(E)-(1R,3S)-2,2-dimethyl-3-(2-oxothiolob-3-ylidenemethyl) cyclopropane carboxylate;

(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, fensulfothion, fonofos, phorate, phoxim, pyrimiphos-methyl, fenitrothion or diazionon;
(c) Carbamates (including aryl carbamates) such as pirimicarb, cloethocarb, carbofuran, ethiofencarb, aldicarb, thiofurox, carbosulfan, beniocarb, fenobucarb, propoxur or oxamyl;
(d) Benzoyl ureas such as triflumeron, or chlorofluazuron;
(e) Organic tin compounds such as cyhexatin, fenbutatin oxide, azocyclotin;
(f) Macrolides such as avermectins or milbemyins, for example such as avamectin, avermectin, and milbemycin;
(g) Hormones such as pheromones;
(h) Organochlorine compounds such as benzene, hexachloride DDT, chlordane or dieldrin.
(i) Amidines, such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as clofentezine, flubenzimine, hexythiazox and tetradifon, moltilicides such as dichofol on propargite, acaricides such as bromopropylate, chorobenzilate, or growth regulators such as hydramethylon, cyromazin, methoprene, chlorofluazuron and diflubenzuron may also be included in the compositions.

Examples of suitable insecticide synergists for use in the compositions include piperonyl butoxide, sesamax, and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S.

The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The compounds of formula (I) and compositions comprising them have shown themselves active against a variety of insect and other invertebrate pests. They are particularly useful in controlling public health pests as flies and cockroaches. They may also be active against organophosphate and pyrethroid resistant strains of pests such as houseflies (Musca domestica). They may be effective in combating both susceptible and resistant strains of the pests in their adult, larval and intermediate stages of growth, and may be applied to the infested host animal by topical, oral or parenteral administration.

The following Preparations and Examples are given by way of illustration.

Preparation 1

This description illustrates the preparation of 4-pentafluoroethyl-2-thiouracil.

Thiourea (3 g) was added to a solution of sodium methoxide in methanol (previously prepared by adding sodium metal (1.089 g) to dry methanol (20 ml)) This was followed by ethyl pentafluoropropionyl acetate (9.61 g) and the reaction mixture was heated under reflux for 3 days. After cooling the solvent was evaporated, in vacuo, to give a brown solid, which was acidified with dilute aqueous hydrochloric acid and extracted with diethyl ether. The combined organic extracts were dried, and removal of the solvent by evaporation, under reduced pressure, gave 4-pentafluoroethyl-2-thiouracil (4.14g), which was immediately carried to the next stage;

'H NMR (CDCl$_3$) 12.3(1H, brs), 11.65 (1H, brs) and 6.2 (1H,s).

Preparation 2

This description illustrates the preparation of 4-pentafluoroethylpyrimidin-6-one. Raney Nickel (0.83g, of a 50% dispersion in water) which was added to a suspension of 4-pentafluoroethyl-2thiouracil (0.5 g) in a mixture of concentrated agueous ammonia (0.23 ml) in water (6 ml). The reaction mixture was heated to reflux for 5.5 hours, cooled, stood overnight, and filtered hot through hyflo. The filtrate was concentrated by evaporation of the solvent under reduced pressure to give the desired compound as a pale green solid. Sublimation (100° C., 0.1 mbar) gave 4-pentafluoroethylpyrimidin-6-one as a white solid mpt 122–126° C.;

'H NMR (CDCl$_3$) 13.05 (1H, brs), 8.30 (1H,s) and 6.94 (1H,s).

Preparation 3

This description illustrates the preparation of 5-bromo-4-trifluoromethylopyrimidin-6-one.

Bromine (4.62 g) was added in one portion to a stirred solution of 4-trifluoromethylpyrimidin-6-one (4.3 g) and sodium acetate (10.53 g) in acetic acid (43 ml). After stirring for 2 hours, the reaction mixture was left to stand for a period of 3 days, after which time it was heated to 80° C. for 1 hour. After cooling to the ambient temperature (ca 22° C.), the solvent was evaporated under reduced pressure. The resultant orange solid was dissolved in ethyl acetate, and washed several times with water. The combined agueous washings were extracted with ethylacetate, and the combined organic layers were washed with aqueous sodium thiosulphate solution, followed by aqueous sodium bicarbonate solution and brine. After drying over magnesium sulphate, evaporation of the solvent under reduced pressure gave 5-bromo-4-trifluoromethylpyrimidin-6-one as white solid (4.8 g, mpt 226-227° C.); H NMR (CDCl3), 8.05(s); 19 NMR (CDCl3), -67.4(s). Preparation 4

This description illustrates the preparation of 3-cyano-5-trifluoromethyl-2-pyridone.

A solution of 3-formyl-5-trifluoromethyl-2-pyridone (3.5 g), hydroxylamine hydrochloride (1.42 g) and sodium formate (1.39 g) in 98% formic acid (42 ml) was heated to reflux for a period of 20hrs. After cooling to ambient temperature, the reaction mixture was poured into water, and rigorously extracted with ethyl acetate. The combined organic extracts were washed with saturated aqueous sodium bicarbonate solution, followed by brine, and dried over anhydrous magnesum sulphate. Removal of the solvent under reduced pressure gave 3-cyano-5-trifluoromethyl-2pyridone as an off-white solid (m.p. 170–175° C.) which was used without further purification. The compound showed (DMSO) 8.54 (1H,d) 8.30 (1H,d).

Preparation 5

This description illustrates the preparation of 2-chloro-3-cyano-5-trifluoromethylpyridine.

A mixture of 3-cyano-5-trifluoromethylpyrdine-2-pyridone (250 mg), phosphorus pentachloride (550 mgs) and phosphonylchloride (0.62 ml) were heated at the reflux temperature for 8 hours. After cooling to ambient temperature (ca 28° C.) the reaction mixture was poured into ice/water and rigourously extracted with ethylacetate. The combined organic layers were washed with aqueous sodium bicarbonate solution followed by brine, and finally dried over anhydrous magnesium sulphate. Removal of the solvent by evaporation under reduced pressure gave 2-chloro-3-cyano-5trifluoromethyl-pyridine as an off-white solid which was used without further purification. The compound showed (CDCl$_3$) 8.89 (1H,d) 8.28 (1H,d).

EXAMPLE 1

This example illustrates the preparation of 1-(3-chloro-5-trifluoromethyl-2-pyridyl)-4-trifluoromethylpyrimidi n-6-one (Compound 1 in Table I).

A dry reaction flask was purged with nitrogen and charged with a 50% suspension of sodium hydride (222 mg). The sodium hydride was washed with pentane and suspended in dimethylformamide (DMF, 4 ml). A solution of 6-trifluoromethylpyrimidin-4-one (758 mg) in DMF (2 ml) was added dropwise. When the addition was complete the reaction was stirred for a further fifteen minutes, then 3-chloro-2-fluoro-5-trifluoromethylpyridine (1.04 g) was added in one portion and the mixture heated at 90° C. for 16 hours. The reaction mixture was allowed to cool, poured into brine, and extracted with ethyl acetate. The organic layer was washed with brine, dried over magnesium sulphate and evapourated in vacuo to give a brown residue which was purified by chromatography on silica gel using 20% diethyl ether/petrol as eluent. The desired product (compound 1 was isolated mp 150.5–153/2° C.

NMR δ(CDCl$_3$) 8.85 (1H,s), 8.24 (1H,s) 8.32 (1H,s), 6.98 (1H,s).

EXAMPLF 2

The following compounds were prepared according to the general method of Example I from appropriate compounds of formula (II) and formula (III):

(i) 1-(5-trifluoromethyl-2-pyridyl)-4-trifluoromethylpyrimidin-6-one (compound No. 2 in Table I). The compound showed δ(CDCl$_3$): 8.92 (1H,s), 8.89 (1H,s), 8.20 (1H,dq), 8.15 (1H,d), 6.98 (1H,s).

(ii) 1-(5-trifluoromethyl-2-pyridyl)-4-pentafluoroethyl-pyrimidin-6-one (compound No. 5 in Table I). The compound showed δ(CDCl3) 8.91 (1H,s), 8.87 (1H,s), 8.19 (1H,dq), 8.15 (1H,d), 7.00 (1H,s).

(iii) 1-(3-chloro-5-trifluoromethyl-2-pyridyl)-4-pentafluoromethylpyrimidin-6-one (compound No. 6 Table I). The compound showed δCDCl$_3$): 8.85 (1H,s), 8.29 (1H,s), 8.20 (1H,s), 7.00 (1H,s).

(iv) 1-(3-dichloromethyl-5,6-dichloro-2-pyridyl-4-trifluoromethylpyrimidin-6-one (compound No. 8 in Table I). The compound showed δ(CDCl₃): 8.99 (1H,s), 8.05 (1H,s), 7.03 (1H,s), 6.54 (1H,s).

(v) 1-(3-cyano-5-trifluoromethyl-2-pyridyl)-4-trifluoromethylpyrimidin-6-one (compound No. 11 in Table I). The compound showed δ(CDC13) 9.13 (1H,s), 8.52 (2H, br.s), 7.01 (1H,s).

(vi) 1-(3-bromo-5-trifluoromethyl-2-pyridyl)-4-trifluoromethylpyrimidin-6-one (compound No. 12 in Table I). The compound showed δ(CDC13) 8.89 (1H, br.s), 8.39 (1H, br.s), 8.25 (1H,s), 6.97 (1H,s).

(vii) 1-(3-bromo-5-trifluoromethyl-2-pyridyl-4- o pentafluoromethylpyrimidin-6-one (compound No. 13 in Table I). The compound showed δ(CDC13) 8.89 (1H, br.s), 8.39 (1H, br.s), 8.25 (1H,s), 7.03 (1H,s).

EXAMPLE 3

This Example illustrates the preparation of 1-(3-nitro-5-trifluoromethyl-2-pyridyl)-4-trifluoromethylpyrimidin -6-one (compound No. 4 in Table I).

A dry reaction flask was purged with nitrogen and charged with a 50% suspension of sodium hydride (0.15 g). The sodium hydride was washed with hexane and suspended in DMF (4 ml). Solid 6-trifluoromethylpyrimidin-6-one (0.5 g) was added portion wise, the mixture stirred for a further 30 minutes, and then 2-chloro-3-nitro-5-trifluoromethylpyridine (1.38 g) was added in one portion. The dark brown reaction mixture was vigourously stirred for 5 hours and then poured into water, acidified with 2M aqueous hydrochloric acid, and extracted rigorously with ethyl acetate. The combined ethereal layer were washed with water, then brine, and dried over magnesium sulphate. The solvent was removed under reduced pressure to afford a brown residue which was subjected to column chromatography using petroleum ether (boiling range 40-60° C.) containing 20% by volume ethylacetate as eluent to give 1-(3-nitro-5-trifluoromethyl-2-pyridyl -4-trifluoromethylpyrimidin-6-one. The compound showed (CDC13) 9.15 (1H,s), 8.78 (1H,s), 8.67 (1H,s), 6.90 (1H,s).

EXAMPLE 4

The following compounds were prepared according to the general method of Example 3 from appropriate compounds of formula II and formula III.

(i) 1-(3-nitro-5-trifluoromethyl-2-pyridyl)-3-bromo-4-trifluoromethylpyrimidin-6-one (compound No. 3 in Table I). The compound showed (CDCl₃) 9.15 (1H,s), 8.79 (1H,s), 8.60 (1H,s).

EXAMPLE 5

The Example illustrates the preparation of 1-(5-trifluoromethyl-2-pyridyl)-3-bromo-4-trifluoromethylpyrimidin -6-one (compound No 7 in Table I).

Bromine (0.15 ml) was added in one portion to a suspension of 1-(5-trifluoromethyl-2-pyridyl)-4-trifluoromethylpyrimidin-6-one (compound No. 2 in Table I) (0.5 g) and sodium acetate trihydrate (1.1 g) in acetic acid (4.8 ml). After stirring for 16 hours, the solvent, was removed under reduced pressure, and the residue was poured into water and aqueous sodium bicarbonate solution. Rigourous extraction into diethylether followed by drying over magnesium sulphate and removal of the solvent under reduced pressure, gave 1-(5-trifluoromethyl-2-pyridyl)-3-bromo-4-trifluoromethylpyrimidin-6-one as a pale yellow solid (m.p. 142-143° C.). The compound showed (CDCl₃) 8.90 (1H,s), 8.80 (1H,s), 8.2 (1H,dg), 8.16 (1H,d).

EXAMPLE 6

The following compounds prepared according to the general method of Example 5. from appropriate compounds of formula (I). (i) 1-(3-chloro-5-trifluoromethyl-2-pyridyl)-3-bromo-4-trifluoromethylpyrimidin-6-one (compound No. 9 in Table I). The compound showed (CDCl₃) 8.85 (1H,br.s), 8.25 (1H, br.s), 8.20 (1H,s).

(ii) 1-(3-chloro-5-trifluoromethyl-2-pyridyl-3-bromo-4-pentafluoroethylpyrimidin-6-one (compound No. 10 in Table I). The compound showed 8.85 (1H, br.s), 8.26 (1H, br.s), 8.19 (1H,s).

The activity of the compounds of formula (I) was determined using a variety of insect pests. The compound was used in the form of liquid preparations containing 500 or 1000 parts per million (ppm) by weight of the compound. The preparations were made by dissolving the compound in acetone and diluting the solutions with water containing 0.01% by weight of a wetting agent sold under the trade name "SYNPERONIC" NX until the liquid preparations contained the required concentration of the Product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

The results of the tests are given in Table II for the compounds, at the rate in parts per million given given in the second column as a grading of mortality designated as 9, 5 or 0 wherein 9 indicates 80–100% mortality, 5 indicates 50–79% mortality and 0 indicates less than 50% mortality.

In Table III the pest organism used is designated by a letter code and the pest species, the support medium or food, and the type and duration of test is given.

TABLE II

| COMPOUND | RATE OF APPLICATION ppm | MD | BG | HV | SPE |
| --- | --- | --- | --- | --- | --- |
| 1 | 500 | 9 | 9 | 0 | 0 |
| 2 | 1000 | 9 | 0 | 9 | 9 |
| 3 | 1000 | 5 | 0 | 0 | 5 |
| 4 | 1000 | 0 | 0 | 0 | 5 |
| 5 | 500 | 5 | 0 | 5 | 5 |
| 6 | 500 | 9 | 9 | 0 | 9 |
| 7 | 500 | 0 | 0 | 5 | 9 |
| 9 | 500 | 0 | 0 | 0 | 9 |
| 10 | 500 | 0 | 0 | 0 | 5 |
| 11 | 100 | 9 | 9 | 0 | 5 |
| 12 | 1000 | 9 | 9 | 0 | 9 |
| 13 | 1000 | 9 | 9 | 0 | 0 |

TABLE III

| CODE LETTERS (TABLE III) | TEST SPECIES | SUPPORT MEDIUM/ FOOD | TYPE OF TEST | DURATION (DAYS) |
| --- | --- | --- | --- | --- |
| BG | *Blattella germanica* (Cockroach nymphs) | Plastic pot/ calf weenes pellets | RT | 2 |
| MD | *Musca domestica* (houseflies adults) | Cotton wool/ sugar | CT | 3 |
| HV | *Heliothis* | Cotton leaf | RT | 2 |

TABLE III-continued

| CODE LETTERS (TABLE III) | TEST SPECIES | SUPPORT MEDIUM/ FOOD | TYPE OF TEST | DURATION (DAYS) |
|---|---|---|---|---|
| SPE | virescens Spodotera exigua (lesser army worm lavae) | Cotton leaf | RT | 2 |

What is claimed is:

1. A compound of formula (I):

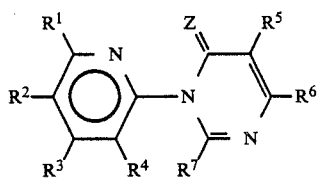

wherein $R^1$ and $R^3$ are independently selected from hydrogen; halogen; nitro; cyano; or lower alkyl, lower alkoxy, lower alkylthio or cycloalkyl any of which can be optionally substituted by halogen;

$R^2$ is hydrogen; halogen; nitro; cyano; lower alkyl, lower alkoxy or lower alkylthio any of which may be optionally substituted with halogen; or $S(O)_nR^8$, where $R^8$ is lower alkyl, halo lower alkyl or cycloalkyl and n is 0, 1 or 2;

$R^4$ is hydrogen; halogen; nitro; cyano; or lower alkyl, lower alkoxy or lower alkythio any of which may be optionally substituted with halogen;

$R^5$ is hydrogen; halogen; nitro; cyano; lower alkyl, lower alkoxy, lower alkylthio any of which can be optionally substituted with halogen; or $NR^9 R^{10}$ where $R^9$ and $R^{10}$ are independently selected from hydrogen, lower alkyl or cycloalkyl;

$R^6$ is hydrogen; halogen; nitro; cyano; lower alkyl, lower alkoxy or lower alkylthio any of which can be optionally substituted with halogen; or $S(O)_nR^8$;

$R^7$ is hydrogen; halogen; nitro; cyano; lower alkyl; lower alkoxy or lower alkylthio any of which is optionally substituted with halogen; $S(O)_nR^8$; or $NR^9R^{10}$; and Z is oxygen or sulphur.

2. A compound according to claim 1 where $R^1$, $R^2$, $R^3$, $R^4$, $R^5$, $R^6$ and $R^7$ are independently selected from hydrogen; halogen; nitro; cyano; or lower alkyl, lower alkoxy or lower alkylthio any of which can be optionally substituted by halogen.

3. A compound according to claim 1 or claim 2 wherein Z is oxygen.

4. A compound according to claim 1; and wherein $R^2$ is halogen or lower alkyl substituted by halogen.

5. A compound according to claim 1; and wherein $R^6$ is halogen or lower alkyl substituted by halogen.

6. A process for preparing a compound of formula (I) as defined in claim 1 which process comprises reacting, in the presence of a solvent and a base, a compound of formula (II)

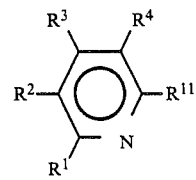

wherein $R^1$, $R^2$, $R^3$ and $R^4$ are as defined in formula (I) and $R^{11}$ is a leaving group selected from fluoro, chloro, bromo, iodo, triflate, mesylate or tosylate; with a compound of formula (III)

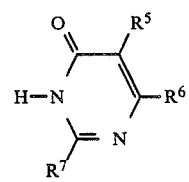

wherein $R^5$, $R^6$ and $R^7$ are as defined in formula (I).

7. A method of killing or controlling insect pests which method comprises applying to the pest or to a locus thereof an effective amount of a compound of formula (I) as defined in claim 1.

8. An insecticidal composition comprising an effective amount of a compound of formula (I) as defined in claim 1 in combination with a diluent or carrier.

9. A compound of formula (IV)

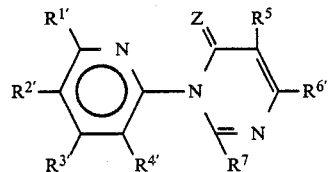

wherein $R^1$ and $R^3$ are independently selected from amino; hydrogen; halogen; nitro; cyano; or lower alkyl, lower alkoxy, lower alkylthio or cycloalkyl any of which can be optionally substituted by halogen;

$R^2$ is amino; hydrogen; halogen; nitro; cyano; lower alkyl, lower alkoxy or lower alkylthio any of which may be optionally substituted with halogen; or $S(O)_nR^8$, where $R^8$ is lower alkyl, halo lower alkyl or cycloalkyl and n is 0, 1 or 2;

$R^4$ is amino; hydrogen; halogen; nitro; cyano; or lower alkyl, lower alkoxy or lower alkythio any of which m ay be optionally substituted with halogen;

$R^5$ is hydrogen; halogen; nitro; cyano; lower alkyl, lower alkoxy, lower alkylthio any of which can be optionally substituted with halogen; or $NR^9 R^{10}$ where $R^9$ and $R^{10}$ are independently selected from hydrogen, lower alkyl or cycloalkyl;

$R^6$ is amino; hydrogen; halogen; nitro; cyano; lower alkyl, lower alkoxy or lower alkylthio any of which can be optionally substituted with halogen; or $S(O)_nR^8$;

$R^7$ is hydrogen; halogen; nitro; cyano; lower alkyl; lower alkoxy or lower alkylthio any of which is optionally substituted with halogen; $S(O)_nR^8$; or $NR^9R^{10}$; and Z is oxygen or sulphur;

provided that at least $R^6$ is amino.

* * * * *